(12) United States Patent
Yurt et al.

(10) Patent No.: US 9,983,260 B2
(45) Date of Patent: May 29, 2018

(54) DUAL-PHASE INTERFEROMETRY FOR CHARGE MODULATION MAPPING IN ICS

(71) Applicant: TRUSTEES OF BOSTON UNIVERSITY, Boston, MA (US)

(72) Inventors: Abdulkadir Yurt, Brighton, MA (US); Selim M. Unlu, Boston, MA (US); Bennett B. Goldberg, Newton, MA (US); Euan Ramsay, Dublin, CA (US)

(73) Assignee: THE UNITED STATES OF AMERICA AS REPRESENTED BY THE SECRETARY OF THE AIR FORCE, Washington, DC (US)

( * ) Notice: Subject to any disclaimer, the term of this patent is extended or adjusted under 35 U.S.C. 154(b) by 81 days.

(21) Appl. No.: 14/433,732

(22) PCT Filed: Oct. 11, 2013

(86) PCT No.: PCT/US2013/064561
§ 371 (c)(1),
(2) Date: Apr. 6, 2015

(87) PCT Pub. No.: WO2014/059287
PCT Pub. Date: Apr. 17, 2014

(65) Prior Publication Data
US 2015/0276864 A1    Oct. 1, 2015

Related U.S. Application Data

(60) Provisional application No. 61/713,218, filed on Oct. 12, 2012.

(51) Int. Cl.
*G01R 31/308* (2006.01)
*G01R 31/311* (2006.01)
(Continued)

(52) U.S. Cl.
CPC ........ *G01R 31/311* (2013.01); *G01B 9/02001* (2013.01); *G01N 21/1717* (2013.01); *G01N 21/41* (2013.01); *G01R 1/071* (2013.01); *G01R 31/26* (2013.01); *G01R 31/2601* (2013.01); *G01R 31/2851* (2013.01); *G01N 2021/1719* (2013.01)

(58) Field of Classification Search
CPC .... G01R 1/071; G01R 31/26; G01R 31/2601; G01R 31/2851; G01R 31/308; G01R 31/311
USPC ......... 324/71, 378, 403, 415, 425, 500, 537, 324/754.01, 754.21, 754.23
See application file for complete search history.

(56) References Cited

U.S. PATENT DOCUMENTS

| | | | | |
|---|---|---|---|---|
| 5,378,509 A | * | 1/1995 | Achreiner | B23K 26/0823 427/271 |
| 6,252,222 B1 | | 6/2001 | Kasapi et al. | |

(Continued)

*Primary Examiner* — Jermele M Hollington
*Assistant Examiner* — Raul Rios Russo
(74) *Attorney, Agent, or Firm* — Preti Flaherty Beliveau & Pachios LLP

(57) ABSTRACT

A dual-phase interferometric method and device for charge modulation mapping in integrated circuits provides significant improvement in signal to noise ratio over conventional detection configurations. The method and device can be used for failure analysis and testing of advanced technology IC chips for which high sensitivity in modulation mapping is required.

32 Claims, 8 Drawing Sheets

(51) Int. Cl.
    *G01R 31/26*     (2014.01)
    *G01R 1/07*     (2006.01)
    *G01N 21/17*     (2006.01)
    *G01N 21/41*     (2006.01)
    *G01B 9/02*     (2006.01)
    *G01R 31/28*     (2006.01)

(56) References Cited

U.S. PATENT DOCUMENTS

| | | |
|---|---|---|
| 6,462,827 B1 | 10/2002 | Frankel |
| 6,496,261 B1 | 12/2002 | Wilsher et al. |
| 7,064,568 B2 | 6/2006 | Hunt et al. |
| 7,450,245 B2 | 11/2008 | Woods et al. |
| 2005/0168212 A1* | 8/2005 | Hunt .................... G01R 31/311 324/750.11 |
| 2005/0222625 A1* | 10/2005 | Laniado ................ A61N 2/02 607/2 |
| 2007/0002328 A1* | 1/2007 | Woods ................ G01R 31/308 356/489 |
| 2007/0018662 A1* | 1/2007 | Pfaff .................... G01R 15/241 356/496 |
| 2008/0186580 A1* | 8/2008 | Pfaff .................... G01R 15/241 359/577 |
| 2009/0272906 A1* | 11/2009 | Gratton .................... G01T 3/00 250/370.05 |
| 2010/0044591 A1* | 2/2010 | Loopstra ............. G03F 7/70033 250/492.2 |
| 2010/0091292 A1* | 4/2010 | Pfaff .................... G01R 15/241 356/457 |
| 2012/0008714 A1* | 1/2012 | Rizwan ................ A61B 5/0031 375/295 |
| 2012/0075601 A1* | 3/2012 | Den Boef ............... G01N 21/47 355/67 |

* cited by examiner

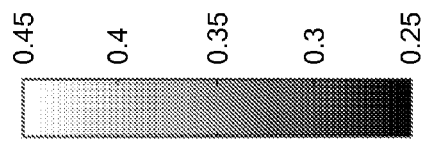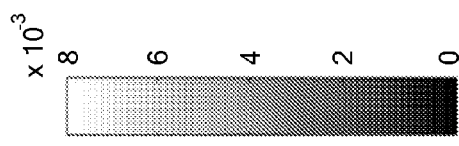
*FIG. 4A*  *FIG. 4B*
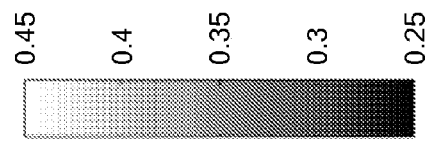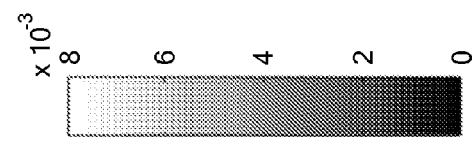
*FIG. 4C*  *FIG. 4D*

FIG. 10A FIG. 10B
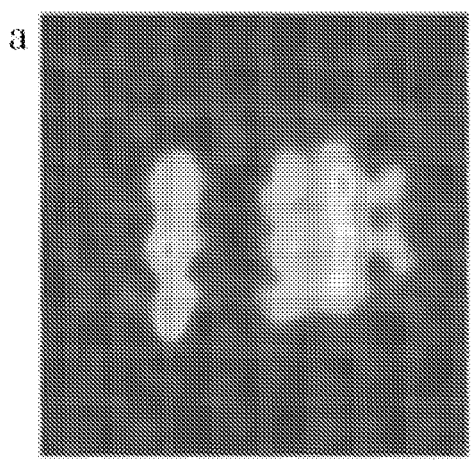 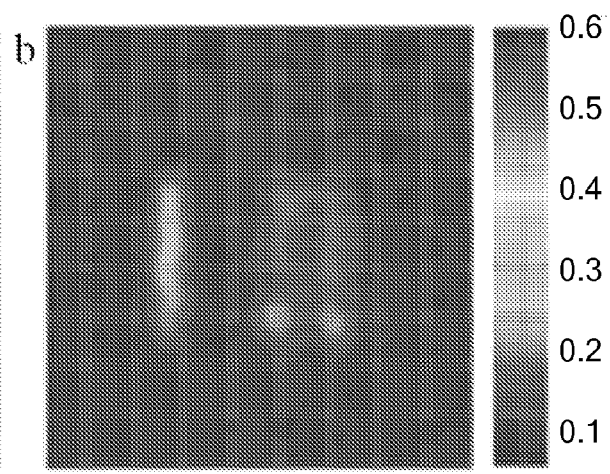
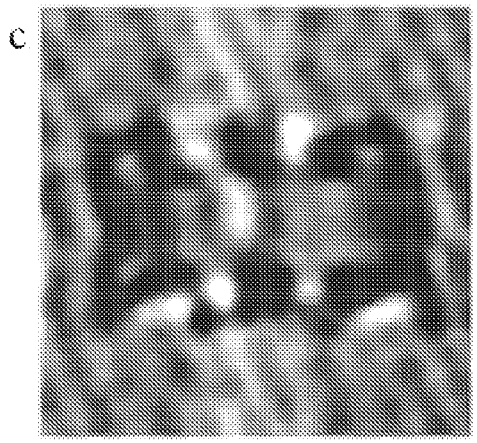 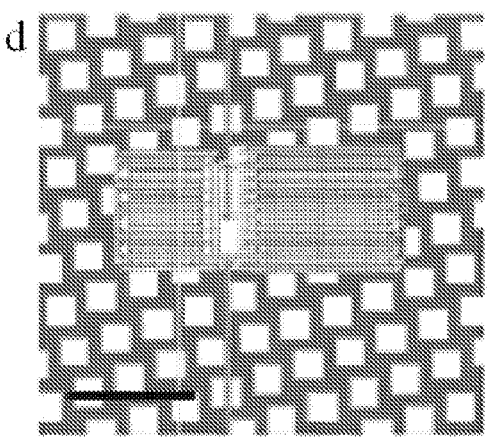
FIG. 10C FIG. 10D

DUAL-PHASE INTERFEROMETRY FOR CHARGE MODULATION MAPPING IN ICS

CROSS REFERENCE TO RELATED APPLICATIONS

This application claims the priority under 35 U.S.C. § 119(e) of U.S. Provisional Application No. 61/713,218, filed Oct. 12, 2012 and entitled Dualphase Interferometry For Charge Modulation Mapping In ICs, the disclosure of which is incorporated by reference herein.

STATEMENT REGARDING FEDERALLY SPONSORED RESEARCH OR DEVELOPMENT

This invention was made with Government Support under Contract No. FA8650-11-C-7102 awarded by the Air Force Research Laboratory. The Government has certain rights in the invention.

BACKGROUND OF THE INVENTION

In-situ monitoring and mapping of electrical activity of devices play an important role in test and fault analysis of integrated circuits (ICs). As front-side access for probing is practically limited due to the increased metallization and packaging, back-side laser-beam techniques have been widely used to investigate transient changes of charge density in the vicinity of the devices [1, 3, 5]. The presence of free-carriers alters the local refractive index and thus influences the intensity of the focused laser beam reflected from the device. However, the amplitude of the reflectance modulation is typically on the order of parts per million of the reflected beam, rendering it a challenge to perform sensitive and quantitative measurements [9]. Further, the technical complications associated with advancing manufacturing technology such as increasing substrate doping levels and decreasing feature size and supply voltage will necessitate even higher detection sensitivity and signal localization capability.

SUMMARY OF THE INVENTION

The present invention provides for in-situ monitoring and mapping of electrical activity of devices in test and fault analysis of integrated circuits (ICs). A device and method are provided that compensate for the amplitude of the reflectance modulation being typically on the order of parts per million of the reflected beam intensity and for the large intensity difference between the applied radiation and the signal component in the information containing radiation reflected from the IC under study. The device and method compensate for the technical complications associated with advancing manufacturing technology such as increasing substrate doping levels and decreasing feature size and supply with higher detections sensitivity and localization capability. The applied radiation is sampled to provide a reference beam. Optics are provided to adjust phase and polarization in the reflected and reference beams with the result being plural beams with polarization and retardation properties. The resulting beam are detected to provide an indication of electrical activity in the IC with enhanced resolution.

The following are also contemplated as embodiments of the invention.

A method for detecting electrical activity in an electrically energized IC substrate comprising the steps of: applying laser radiation to the substrate; receiving radiation from said substrate representative of the radiation applied thereto; optically processing the received radiation to provide two beams of radiation with different phase angles therebetween; sensing the intensity of the two beams; and electronically processing the sensed beams to provide an indication of the electrical activity of the substrate.

A method wherein the applying step applies linearly polarized infrared CW laser radiation.

A method wherein the applying step applies the radiation to a two dimensional area of the substrate.

A method wherein the applying step includes scanning the radiation for application to the substrate.

A method including the step of electrically energizing the substrate at timing determined by a clock.

A method wherein the applying step applies the radiation through an aSIL lens.

A method wherein the receiving step includes receiving the radiation through the aSIL.

A method wherein the radiation received from said substrate includes components representative of effects from the electrical energization of the substrate at a level many orders of magnitude below other components in the received radiation.

A method wherein the phase angles of the optically processed radiation differ by $\pi/2$.

A method wherein the step of optically processing includes providing one of the beams as a reference beam by passing the reference beam through one or more of a 45 degree quarter wave plate and a zero degree polarizer followed by reflection back through the one of more of the quarter wave plate and polarizer with the resulting beam being combined with the other of the two beams.

A method wherein the reference beam after passing through the quarter wave plate and polarizer is sensed with the resulting sensed signal being processed as a part of said electronically processing step.

A method wherein the sensing step includes sensing DC and RF components in the two beams.

A method wherein the electronically processing step includes providing time resolved and DC components.

A method wherein the electronically processing step includes the step of providing a two dimensional image of the effects of electrical energization of the substrate.

An apparatus for detecting electrical activity in an electrically energized IC substrate comprising: a source of polarized radiation; optics for applying the radiation to the substrate and receiving radiation therefrom having a component representative of the electrical activity of the substrate and of background effects; an optical system responsive to the received radiation for providing two beams of phase separated radiation representative of the received radiation; means for sensing the two beams to provide respective signals therefrom; means for processing the sensed beams to provide an indication of the electrical activity of the substrate separate from the background effects.

An apparatus wherein the radiation source includes a laser.

An apparatus wherein the laser is a linearly polarized infra-red CW laser.

An apparatus wherein the optics includes an aSil.

An apparatus wherein the optics includes a beam splitter arranged to apply the laser radiation to the substrate and to the optical system and to receive radiation from the substrate for application to the optical system.

An apparatus wherein the optical system includes: reference optics receiving a reference portion of the radiation from the substrate to provide a reference beam; and combining optics for combining the reference beam and the radiation received from the substrate for application to the sensing means.

An apparatus wherein the reference optics includes a quarter wave plate and a polarizer.

An apparatus wherein the reference optics includes reflecting means for causing the reference portion of the radiation from the substrate to be reflected back through the polarizer and the quarter wave plate to the combining optics.

An apparatus wherein the quarter wave plate is aligned to 45 degrees and the polarizer is aligned to zero degrees.

An apparatus wherein the radiation from the substrate has a first component unresponsive to the effects of the electrical energization of the substrate at an intensity orders of magnitude greater than a second component therefrom that represents the energization and the optical system provides in the beam applied to the sensing system characteristics that distinguish the first and second components.

An apparatus wherein the processing means provides separate signals for the first and second components.

An apparatus including 2D means for causing the radiation received from the substrate to represent a two dimensional area of the substrate.

An apparatus wherein the 2D means includes scanning means.

An apparatus wherein the processing means includes lock in amplifiers and/or balance detectors providing time resolved and DC components from the sensed radiation.

An apparatus including means for displaying the indication of electrical activity in a two dimensional form.

An apparatus for dual-phase interferometric confocal imaging for electrical signal modulation mapping in ICs comprising: a source of laser radiation; means for dividing said radiation into a beam directed to and reflected from an IC and a reference beam; means for combining said reflected and reference beams; means for adjusting phase and polarization in said reflected and reference beams; and means for detecting the adjusted reflected and reference beams to provide an indication of electrical activity in said IC.

An apparatus for dual-phase interferometric confocal imaging for electrical signal modulation mapping in ICs comprising: means for applying laser radiation to the IC; means for receiving laser radiation reflected from said IC having information representative of electrical activity in said IC; optical processing means responsive to the radiation as applied to said IC and reflected from said IC for creating a plurality of beams having distinct polarization and retardation properties; and means responsive to said plurality of beams for isolation of the information representative of said electrical activity.

An apparatus wherein the means responsive to the plurality of beams for isolation of the information representative of the electrical activity includes one or more lock-in amplifiers.

DESCRIPTION OF THE FIGURES

U.S. Provisional Application No. 61/713,218, filed Oct. 12, 2012 and entitled Dualphase Interferometry For Charge Modulation Mapping In ICs, is incorporated by reference herein.

The invention will be more fully understood from the following detailed description taken in conjunction with the accompanying drawings in which:

FIGS. 4(a)-4(d) show respectively: (a) raw interferometric image of an inverter device (DUT-1) obtained by the detector 44 in FIG. 1; (b) raw interferometric image of an inverter obtained by the detector 46 in FIG. 1; (c) reconstructed image to find $I_s$ using the (a), (b) and a reference intensity image; and (d) reflectance image of the same area without the interferometric device in operation;

FIGS. 10(a) and 10(b) show modulation map images of the first inverter in the "I3" chain with the interferometer method in 10(a) and without the interferometric method in 10(b); FIG. 10(c) shows a DC reflectance image of the device; FIG. 10(d) shows the CAD layout of the device showing the metal-3 filling material in the vicinity of the transistors; the scale bar is 1 micron.

DETAILED DESCRIPTION OF THE INVENTION

Figure 1:
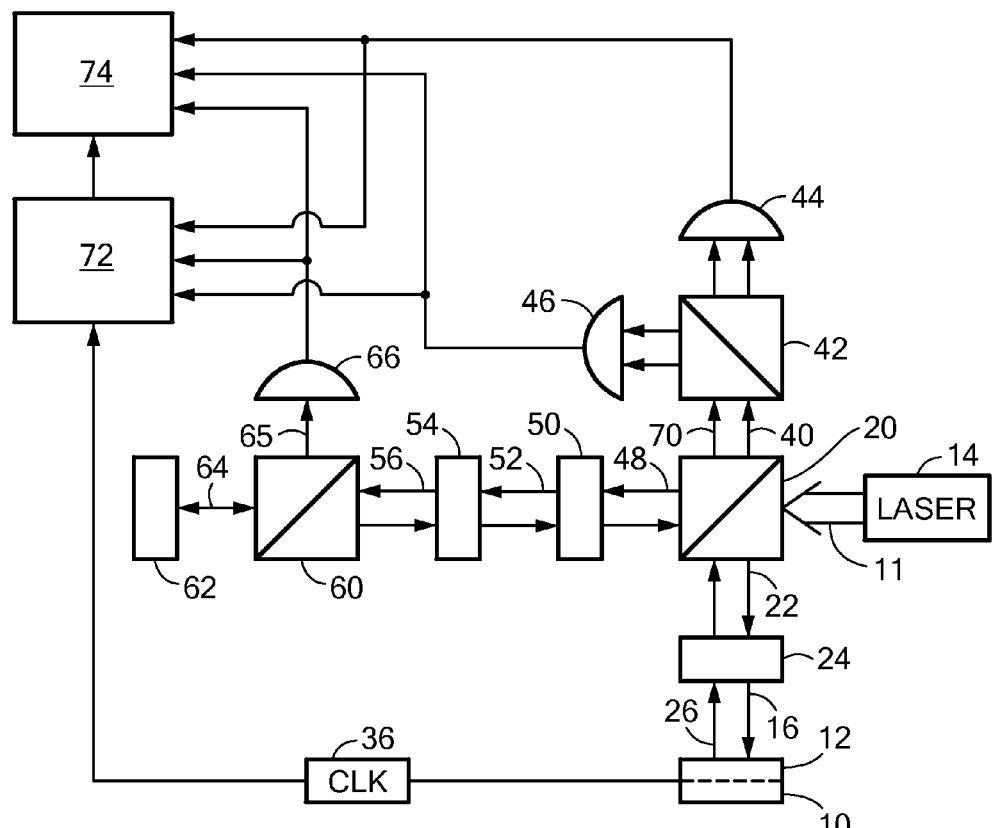
FIG. 1 is a schematic diagram of a dual-phase interferometric confocal imaging device for electrical signal modulation mapping in ICs according to the invention.

A schematic diagram of an embodiment of a device according to the invention is show in FIG. 1 wherein a device 10, typically an IC, and typically an imaging system 12 has light 16 applied to it from a beam 11 of a laser 14 after passing through a non-polarizing beam splitter 20 as a beam 22 and after passing through a polarizer 24 aligned to 45 degrees. A Glan-Taylor polarizer is typically used. Light 26 is reflected from the device 10 to and through the polarizer 24 for use as described below. The laser 14 is typically a continuous wave IR laser with a wavelength of 1340 nm. In one embodiment, the imaging system 12 includes scanning optics, such as raster beam scanning A two-axis galvanometer based mirrors are used to scan the beam on the chips. Alternatively, the system can be implemented without scanning.

Figure 2:
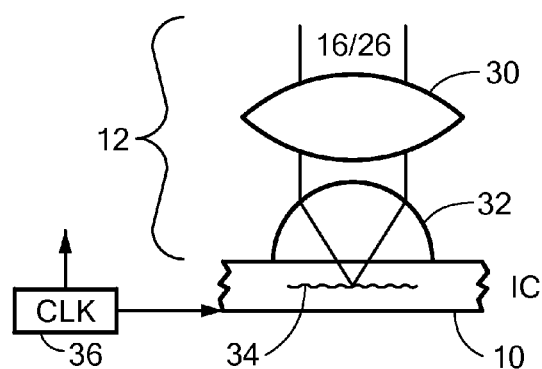
FIG. 2 illustrates a typical use of the invention in analyzing an IC using an aSIL.

FIG. 2 illustrates an exemplary device 10 under test (DUT-1) as an aSIL system in which the laser light 16 is applied through a focusing lens or optics 30 to a SIL lens 32, as is known for example in the art of U.S. Pat. No. 6,687,058, incorporated herein by reference. The light is thus focused to and radiation reflected from an aplanatic region 34 under study within the device or IC 10. A clock 36 represents the activating energy applied to the drive the device 10.

Referring again to FIG. 1, the return beam 26 from the devices 10 and 12 transits the polarizer 24, receiving another 45 degree polarization alignment for a total of 90 degrees, and then passes through the beam splitter 20 without reflection as a beam component 40 which then has one component pass through a polarizing beam splitter 42 for detection by a single-mode-fiber-coupled InGaAs PIN detector 44 and another component reflected by the polarizing beam splitter 42 to a similar PIN detector 46.

The laser beam 11 not reflected by beam splitter 20 passes as radiation 48 through a zero-order quarter wave plate 50 aligned to 45 degrees to exit as a beam 52 and then through a Glan-Taylor polarizer 54 aligned to zero degrees forming beam 56. Light in beam 56 passes through a pellicle beam splitter 60 for reflection by a reference mirror 60 mirror 62 providing incident and reflected beams 64.

The reflected component of beam 64 is reflected by beam splitter 60 as beam 65 to a PIN detector 66. A through component of beam 64 transits the polarizer 54 and the quarter-wave plate 50 to be, in part, reflected by the beam splitter 20 as component 70 which together with component 40 are subject to polarization and beam splitting by beam splitter 42 to which they are applied. The resulting separate light beams, with phase differences of π/2 are applied to PIN detectors 44 and 46 in components with distinct polarization. The outputs of the PIN detectors 44, 46, and 66 are applied to two lock-in amplifiers 72. The data acquisition 74 (signal detection from lock-in amplifiers) is synchronized with the galvanometer mirrors used for scanning, if a scanning implementation is employed, so that the signal at each beam position corresponds to a pixel in the 2D image.

In this configuration a high spatial resolution interferometric confocal imaging results using an aplanatic solid immersion lens system 12 for mapping the time dependent characteristics of electrical signals in an IC chip 10. The interferometric measurement provides superior detection sensitivity with respect to conventional reflectance based carrier modulation based probing techniques. The invention is based on simultaneous dual-phase measurement of interferometric response formed by coherent mixing of the weakly modulated reflected beam 26 with strong reference beams 48, 65 and 70. The amplifiers 72 process these signals according to the processing mathematics shown below. The interferometric mixing not only amplifies the weak signal amplitude but also provides access to the relative phase of the reflected signal through the principle of two-phase measurement.

The light intensity on each detector 44 ($det_1$) and 46 ($det_2$) can be expressed as follows.

$$I_{det1}(t)=I_r+I_s(t)+2\sqrt{I_rI_s(t)}\cos\theta_{rs}(t)$$

$$I_{det2}(t)=I_r+I_s(t)+2\sqrt{I_rI_s(t)}\sin\theta_{rs}(t) \quad (1)$$

where $I_r$, $I_s(t)$ and $\theta_{rs}(t)$ refer to the detected optical intensity of reference beam 70 and sample beam 40 from splitter 20; and the phase angle between the two beams, respectively.

In a typical measurement on IC devices, the intensity reflected from the sample, $I_s$, consists of two components: the topology dependent DC signal and a high-frequency modulation signal (RF) which is due to charge carrier activity. For time-resolved measurements. The two lock-in amplifiers 72 and 74 which are driven by the clock frequency of the IC are used to monitor the RF part of the signal. The RF part of the signal only retains the third terms in Equation 1 since the first term does not have an RF component and the second term is negligible compared to the third term. The amplitude of the time-resolved and DC signals can be found as:

$$I_s(f_{clk})=(I_{det1}^2(f_{clk})+I_{det2}^2(f_{clk}))/4I_r$$

$$I_s(DC)=0.5[I_{det1}+I_{det2}-\sqrt{4I_r(I_{det1}+I_{det2})-(I_{det1}-I_{det2})^2-4I_r^2}] \quad (2)$$

The phase term, $\theta_{rs}(t)$, does not appear in Equation 2 as it is eliminated using two-phase measurements, $I_{det1}$ and $I_{det2}$, these being the detectors 44 and 46.

Figure 3:
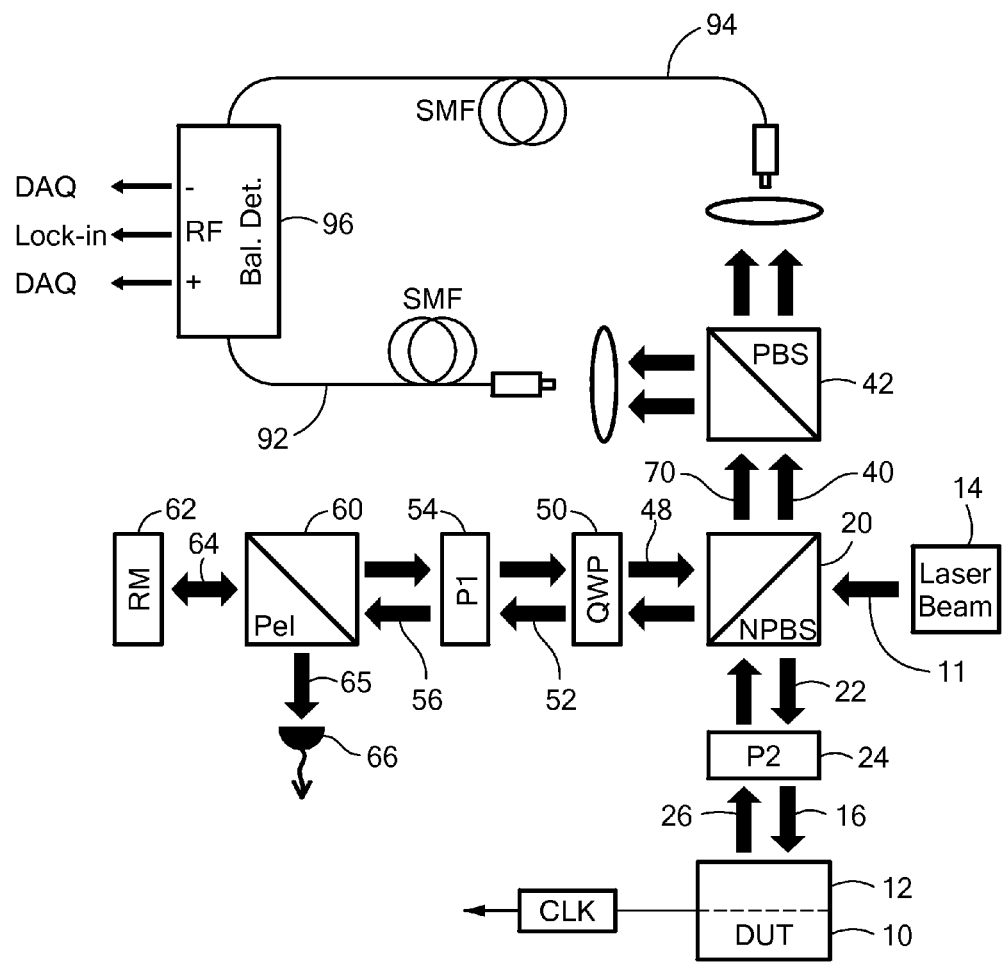
FIG. 3 is a schematic diagram of a further embodiment of a dual-phase interferometric confocal imaging device for electrical signal modulation mapping in ICs.

In a further embodiment, referring to FIG. 3, the two beams from the polarizing beam splitter 42 are coupled into single mode fibers (SMF) 92, 94 that feed the differential inputs of an AC-coupled balanced photodetector 96, such as an InGaAS-PIN photodetector. The reference beam is transformed into a circularly polarized beam with a polarizer and a quarter-wave-late (QWP) after it is reflected from the reference mirror (RM); then the reference beam ($P_{ref}$=0.3 mW) is similarly split into two with a phase difference of π/2 by the polarizing beam splitter (PBS) before being coupled into the same single mode fibers (SMF). The photo-voltage generated on each detector can be expressed as:

$$V_{det1}(t)\propto I_r+I_p(t)+2\sqrt{I_rI_p(t)}\cos\theta_{rp}(t)$$

$$V_{det2}(t)\propto I_r+I_p(t)+2\sqrt{I_rI_p(t)}\sin\theta_{rp}(t) \quad (3)$$

where $I_r$, $I_p(t)$ and $\theta_{rp}(t)$ refer to the detected optical intensity of reference and reflected probe beams and the phase angle between the two beams respectively. The differential output of the balanced detector, $V_{RF}(t)$, retains only the contribution of the interferometric terms:

$$V_{RF}(t)\propto 2\sqrt{I_rI_p(t)}[\cos\theta_{rp}(t)-\sin\theta_{rp}(t)] \quad (4)$$

Note that the amplitude of the signal is amplified by the referenced beam of which intensity can be adjusted independently. Also, the differential detection allows us to eliminate significantly the common-mode noise associated with the large background intensity (first two terms in Eq. (3)). The differential output of the balanced detector is fed into a lock-in amplifier in order to perform heterodyning to decouple the amplitude of the signal ($2\sqrt{I_rI_p(f_{LO})}$) from the contribution of the phase component ($\theta_{rp}(t)$) at the frequency of a local oscillator signal ($f_{LO}$). In the measurements, the local oscillator signal is provided by the test chips in order to obtain the electronic phase maps in addition to the amplitude maps. When the phase maps are not of interest, the internal signal generator of the lock-in amplifier is used to provide the local oscillator.

Although it may not be critical in some or most applications, the signal to noise ratio (SNR) of the DC component of the reflected probe beam intensity that provides the topographical information about the DUT can also be improved through the interferometric mixing. Assuming $I_r \gg I_p$ the DC component can be obtained using the monitor-outputs of the balanced detector:

$$I_p(DC) \propto \sqrt{(V_{det1}-V_{ref})^2+(V_{det2}-V_{ref})^2} \quad (5)$$

where $V_{ref}$ refers to the voltage read on the detector that monitors the reference beam intensity.

As an example, FIGS. 4(a) and 4(b) illustrate the raw interferometric images of an inverter concurrently obtained through $I_{det1}$ and $I_{det2}$, respectively. The topographical features of the devices, typically ICs, are hardly visible due to strong intensity fluctuations over the whole image due to coupling of the phase (sine and cosine terms in Eq. 1). FIG. 4(c) demonstrates the amplitude image ($I_s$) of the devices obtained through processing the images in FIGS. 4(a) and 4(b) according to Eq. 2. The phase coupling is drastically eliminated and the topographic amplitude image of the devices is obtained compared to reflectance image of FIG. 4(d) that is directly obtained by simply blocking the reference arm of the setup.

Figure 5B:
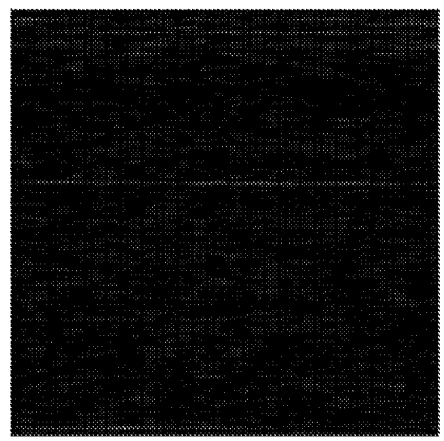
FIGS. 5(a)-5(d) show: (a) a reflectance image of the device layer of the inverted chain for which the layout design is shown in (b); (c) interferometric measurement of free-charge carrier modulation map at clock frequency (25 Mhz); and (d) free-charge carrier modulation map without the interferometric device in operation with no discernible signal.
Figure 5D:
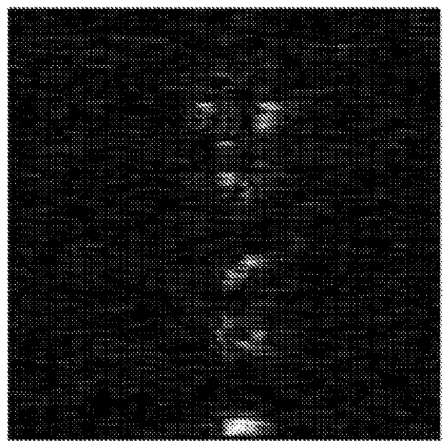
Figure 5A:
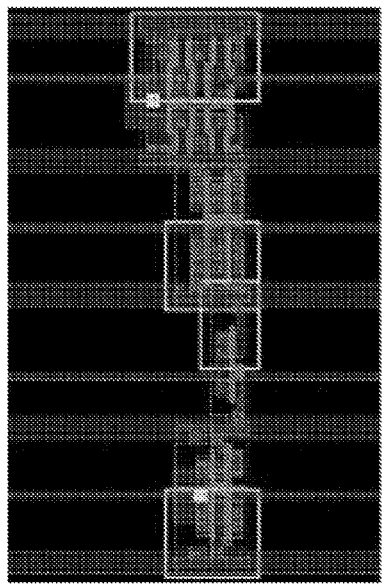
Figure 5C:
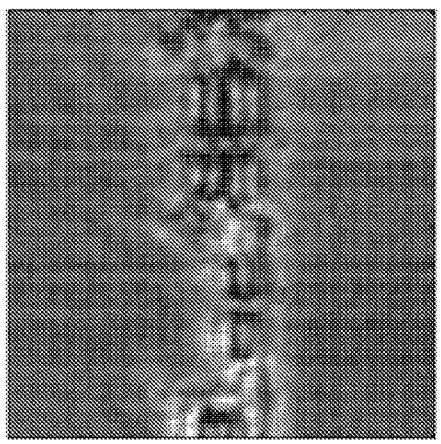

FIGS. 5(a)-5(d) map charge carrier density modulations on the metallic interconnects and transistors of an inverter chain in a test-chip of 180 nm technology. In FIG. 5(a), a confocal reflectance image is provided of the topographic structures for which the layout design is shown in FIG. 5(b). FIG. 5(c) illustrates the electrical activity map at the typical clock frequency, 25 MHz, in the region of interest. The modulation was detected with a high signal to noise ratio for the given chip. In order to demonstrate the improvement in detection limit and sensitivity over conventional modulation mapping techniques based on reflectance measurements, the reference arm of the interferometry in beams 48 and 65 was blocked and then another measurement taken using the same experimental parameters. As FIG. 5(d) shows, no modulation was observed for this case.

Figure 6A:
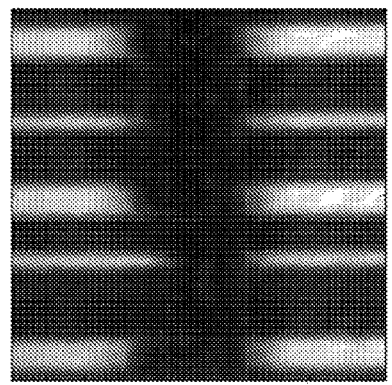
FIGS. 6(a)-6(c) show: (a) A reflectance image of the metal-1 layer of the inverted chain for which the layout design is shown in FIG. 5(b), the metal lines having disappeared in the middle of the image due to presence of devices underneath them (see FIG. 5(a)); (b) The interferometric measurement of free-charge carrier modulation map on the metal lines at clock frequency (25 MHz); and (c) the free-charge carrier modulation map without the interferometric mode with no discernible signal observed.
Figure 6B:
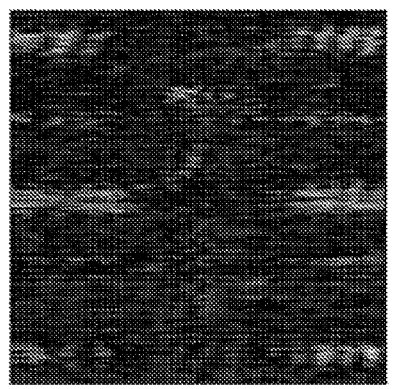
Figure 6C:
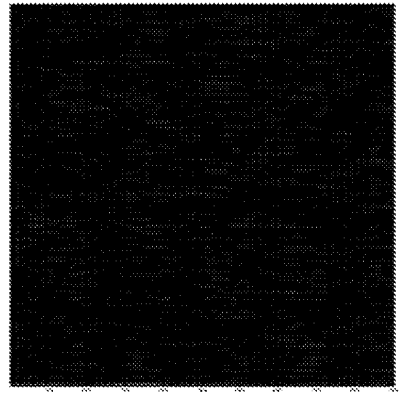

An advantage of the confocal modality is the improved depth resolution and rejection of out of focus light compared to conventional laser scanning and wide-field microscopes. By probing the interconnects that route the electrical signal between the inverters in the chip, FIG. 6(a) shows a confocal reflectance topographic image of a metal-1 plane. The lines are interrupted in the middle of the image due to the presence of the transistors located underneath the interconnect plane about a micron below. FIG. 6(b) illustrates the modulation map at the clock 36 frequency where the signal overlaps on the metal lines. On the other hand the reflectance response shown in FIG. 6(c) at the clock frequency does not provide any discernible signal similar to the previous case. The origin of the signal observed on metal interconnects must lie on a distinct phenomenon relative to the one observed on the transistors. It is known in the art that the change in the free-carrier concentration in silicon is dominantly responsible for the index modulations in the vicinity of the devices. Neither the carrier concentration nor resistive thermal effects is expected on the interconnects in the given frequency regime.

Figure 7A:
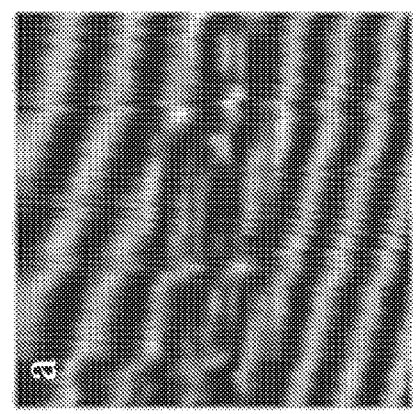
FIGS. 7(a) and 7(b) show the raw images of an inverter device recorded by the monitor-outputs of the balanced detector.
Figure 7B:
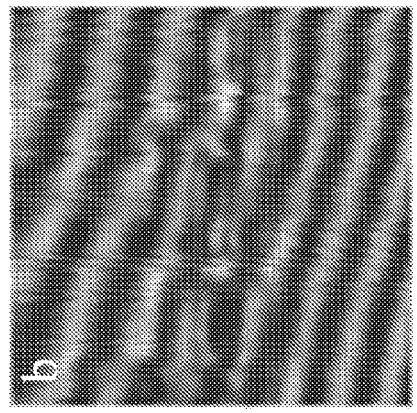
Figure 7C:
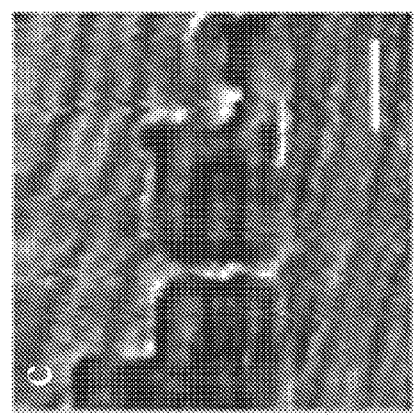
FIG. 7(c) shows reconstructed image to obtain the amplitude image through decoupling the phase contribution using Eq. (5); the length of the scale bar is 2 microns.

FIG. 7(a) and FIG. 7(b) show the images of a part of an inverter chain in a 180 nm technology bulk silicon test-chip (DUT-2) recorded through the two monitor-outputs of the balanced detector of the device shown in FIG. 3. The topographical features of the devices are barely visible due to strong intensity fluctuations over the whole image due to coupling of the phase (sine and cosine terms in Eq. 3). FIG. 7(c) demonstrates the amplitude image $I_p(DC)$ of the devices obtained through processing the images in FIG. 7(a) and FIG. 7(b) according to Eq. (5). The phase coupling is dramatically reduced and the topographic amplitude image of the devices is recovered. The reconstructed image accuracy can be improved by performing a more precise calibration of the detectors.

Figure 8A:
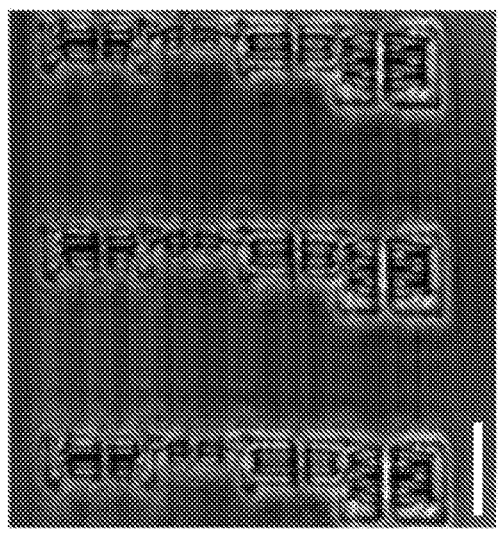
FIG. 8(a) shows a reflectance image of a device under test (DUT-2) obtained without the interferometric mode.
Figure 8B:
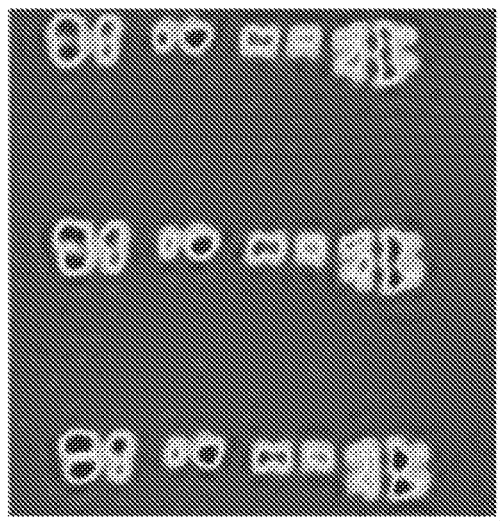
FIG. 8(b) shows the carrier modulation map of DUT-2 at 12.5 MHz using the interferometric mode.

FIG. 8(a) shows a reflectance DC image of the three elements of the inverter chains in the same test chip. Each element contains four inverters built using different unit cells. At first, we studied the free-carrier modulation activity on the inverter chains using our interferometeric method. FIG. 8(b) shows the intensity map of the free-carrier modulation activity at 12.5 Mhz, i.e. the frequency of the input signal fed into the inverter chains. The strong contrast of the modulation map helped us to identify the location of the charge density modulations accurately on the DUT-2.

Figure 8C:
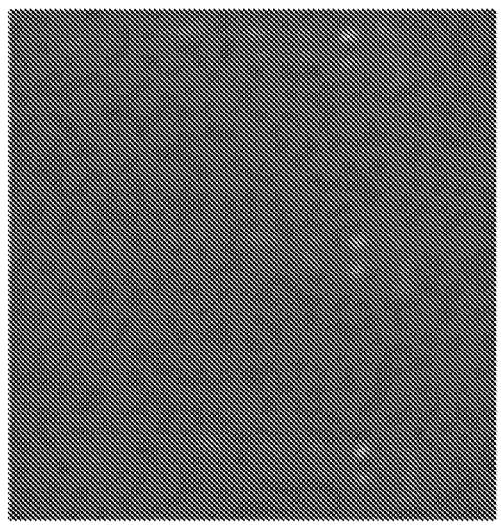
FIG. 8(c) shows the carrier modulation of DUT-2 test at 12.5 MHz without the interferometric mode; the length of the scale bar is 5 microns.

In order to determine the improvement in detection sensitivity, the measurement was performed with the conventional approach for which the reference arm and one of the inputs of the balanced were blocked and the laser power was adjusted so that the comparison was performed at the same probe beam power level. FIG. 8(c) shows the amplitude image of the modulation map obtained with non-interferometric approach. Although the signal was observable for relatively larger structures, the SNR was not adequate to reach to a conclusion about the proper operation of DUT-2. Note that the interferometric mixing provided an SNR about an order of magnitude better for this test chip.

Figure 9A:
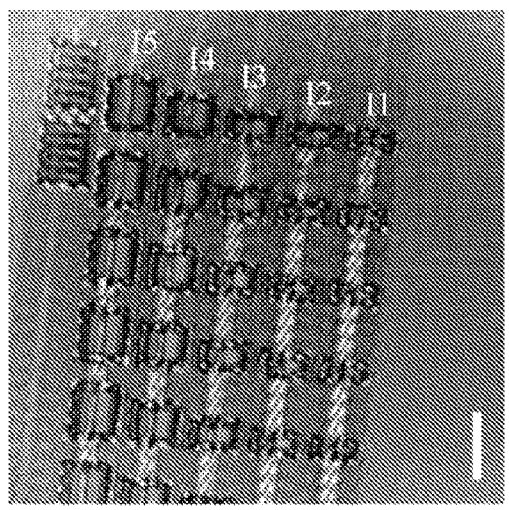
FIG. 9(a) shows a reflectance image of a further device under test (DUT-3) obtained without the interferometric mode.

In a further test, a different test-chip of 32 nm SOI technology (DUT-3) was investigated. FIG. 9(a) shows a reflectance DC image of the end section of the invert chains labeled from "I1" to "I5." The size of the transistors is identical in each chain and it increases from "I1" to "I5." As opposed to DUT-2, this chip contains an insulating oxide layer underneath the active layer; therefore the total internal reflection and the aberrations due to the silicon-silicon dioxide interface reduces the effective NA of the aSIL objective down to ~1.5. Despite the significant reduction of NA, a considerably large SNR for modulation amplitude on the inverter chains at nominal operating conditions ($V_{dd}$=0.9 V) was observed even without the interferometric method. FIG. 4(b) illustrates the amplitude map at 12.5 MHz, i.e., the frequency of the input signals fed into the inverters, without the interferometric mixing. The SNR is sufficiently high to confirm the normal switching behavior on all chains except "I2," which was deactivated in advance to have a negative control unit in DUT-3. Note that the phase map (FIG. 4(c)) illustrates the in-phase and out-of-phase switching activity of the NMOS and PMOS transistors as well as successive inverters in the chains with respect to the signal at the output pin of the "I3" chains which was used as the local oscillator signal for the lock-in amplifier.

The improvement in sensitivity obtained by using the interferometric detection can be seen by comparing FIG. 10(a), made with the interferometric method, and FIG. 10(b), made without the interferometric method. Note that the laser power was reduced about 60% with respect to the earlier measurement on DUT-3 ($P_{probe}$≈0.25 mW after the aSIL) in order to avoid saturation of the lock-in amplifier in the interferometric measurements. At the nominal operating conditions, the interferometric method consistently provided an SNR improvement about a factor of three. The image distortion observed on the modulation maps is believed to be due to the filling structures underneath the devices. The reflectance DC image of the devices for which the CAD layout design is shown in FIG. 10(d) illustrates the present of these filling structures in the vicinity of the device layer and their interference with the image quality (FIG. 5(c))

Figure 9B:
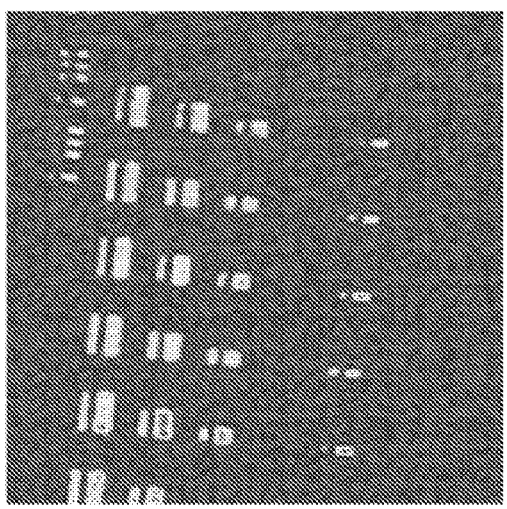
FIG. 9(b) shows the carrier modulation map of the DUT-3 at 12.5 MHz.
Figure 9C:
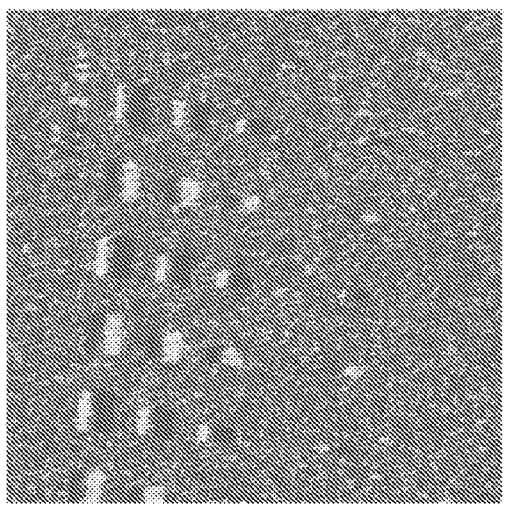
FIG. 9(c) shows the phase map of DUT-3 at 12.5 MHz; both 9(b) and 9(c) are obtained without the interferometric mode; the length of the scale bar is 5 microns.

Under the same experimental conditions, the modulation amplitude was observed to be significantly higher in DUT-3 in comparison with DUT-2 when the interferometric detection was not employed (compare FIG. 8(c) with FIG. 9(b)). The common path-interferometric effect due to the presence of the oxide-box underneath the device layer is believed to play an important role in enhancing the modulation amplitude on the reflected probe beam in DUT-3.

The present invention presents an interferometric imaging technique for spatially mapping of the time dependent electrical activity of devices and metallic interconnects of ICs and other devices with improved sensitivity and localization to address the challenges associated with advanced IC technology nodes. The technique can be used for quantitative analysis of delay/jitter effects in a given part of the circuit through monitoring relative phase of interferometric response with respect to reference clock frequency of the circuitry. Accordingly the invention is not to be limited except according to the following claims.

REFERENCES

1. Kindereit, U., et al., "Comparison of laser voltage probing and mapping results in oversized and minimum size devices of 120 nm and 65 nm technology," Microelectronics Reliability, Vol. 48, No. 8 (2008), pp. 1322-1326.
2. Ng Y. S. et al., "Laser voltage imaging, A new perspective of laser voltage probing," Proc 36$^{th}$ Int'l Symp for Testing and Failure Analysis, Addison, Tex., November 2010, pp. 5-13.
3. Liao, J. Y., et al., "Scan chain failure analysis using laser voltage imaging," Microelectronics Reliability, Vol. 50, No. 9(2010), pp. 1422-1426.
4. Kasapi, S., et al., "Advanced scan chain failure analysis using laser modulation mapping and continuous wave probing," Proc 37$^{th}$ Int'l Symp for Testing and Failure Analysis, San Jose, Calif., November 2011, pp. 12-17.
5. Zachariasse, F., et al., "Laser modulation mapping on an unmodified laser scanning microscope," Microelectronics Reliability, Vol. 50, No. 9 (2010), pp. 1417-1421.
6. Teo, J. K. J. et al., "Characterization of MOS transistors using dynamic backside reflectance modulation technique," Proc 37$^{th}$ Int'l Symp for Testing and Failure Analysis, San Jose, Calif., November 2011, pp. 170-175.
7. Lo, W. K., et al., "Polarization Difference Probing: A New Phase Detection Scheme for Laser Voltage Probing", Proc 30$^{th}$ Int'l Symp for Testing and Failure Analysis, Worcester, Mass., November 2004, pp. 9-17.
8. Wilsher K., et al., "Integrated Circuit Waveform Probing Using Optical Phase Shift Detection", Proc 26$^{th}$ Int'l Symp for Testing and Failure Analysis, Bellevue, Wash., November 2000, p. 479-485.
9. U. Kindereit, G. Woods, T. Jing, U. Kerst, R. Leihkauf, and C. Boit, IEEE Transactions. Device and Materials Reliability, 7, 19, (2007).
10. B. Deutsch, R. Beams, and L. Novotny, Appl. Opt. 49, 4921 (2010).
11. F. H. Köklü, J. I. Quesnel, A. N. Vamivakas, S. B. Ippolito, B. B. Goldberg, and M. S. Ünlü, Opt. Express 16, 9501-9506 (2008).
12. K. A. Serrels, E. Ramsay, and D. T. Reid, Appl. Phys. Lett. 94, 073113 (2009).
13. H. K. Heinrich, D. M. Bloom, B. R. Hemenway, K. McGroddy, and U. Keller, IEEE Trans Electron. Dev., 33 (11), 1860, (1987.)

The invention claimed is:

1. A method for detecting electrical activity in a substrate, wherein the substrate is an electrically energized IC substrate, the method comprising the steps of:
   applying a generated beam of laser radiation to the substrate;
   receiving a reflected beam of radiation from said substrate representative of the generated beam of laser radiation applied thereto;
   optically processing the reflected beam of radiation to provide two beams of radiation with different phase angles therebetween;
   sensing intensities of the two beams of radiation with different phase angles; and
   electronically processing intensities of the two beams to provide an indication of the electrical activity of the substrate.

2. The method of claim 1, wherein said applying step applies linearly polarized infrared CW laser radiation.

3. The method of claim 1, wherein said applying step applies said generated beam to a two dimensional area of said substrate.

4. The method of claim 3, wherein said applying step includes scanning the generated beam for application to said substrate.

5. The method of claim 1, further including the step of electrically energizing the substrate at timing determined by a clock.

6. The method of claim 1, wherein said applying step applies the generated beam through an aSIL lens.

7. The method of claim 6, wherein said receiving step includes receiving said reflected beam through said aSIL.

8. The method of claim 1, wherein the reflected beam includes components representative of effects from the electrical activity of the substrate at a level many orders of magnitude below other components in the reflected beam.

9. The method of claim 1 wherein the phase angles of the two beams of radiation differ by $\pi/2$.

10. The method of claim 1, wherein applying the generated beam of laser radiation to the substrate includes:
    splitting a reference beam from the generated beam of laser radiation prior to applying the generated beam to the substrate;
    passing the reference beam through one or more of a 45 degree quarter wave plate and a zero degree polarizer;
    reflecting the reference beam back through the one of more of the quarter wave plate and polarizer; and
    combining the resulting reference beam with the reflected beam of radiation from said substrate.

11. The method of claim 10, further comprising sensing a portion of said reference beam after having passed through the quarter wave plate and polarizer, and wherein electronically processing the intensities of the two beams includes processing the resulting sensed signal.

12. The method of claim 1, wherein said sensing step includes sensing DC and RF components in the two beams.

13. The method of claim 1, wherein said electronically processing step includes providing time resolved and DC components.

14. The method of claim 1, wherein said electronically processing step includes the step of providing a two dimensional image of the effects of the electrical activity of the substrate.

15. Apparatus for detecting electrical activity in a substrate, wherein the substrate is an electrically energized IC substrate, the apparatus comprising:

a source of polarized radiation;

optics for applying a generated beam of the radiation to the substrate and receiving a reflected beam of radiation therefrom, the reflected beam having a component representative of the electrical activity of the substrate and of background effects;

an optical system responsive to the reflected beam for providing two beams of phase separated radiation representative of the reflected radiation;

means for sensing the two beams to provide respective signals therefrom;

means for processing the sensed beams to provide an indication of the electrical activity of the substrate separate from the background effects.

16. The apparatus of claim 15, wherein said source of polarized radiation includes a laser.

17. The apparatus of claim 16, wherein said laser is a linearly polarized infra-red CW laser.

18. The apparatus of claim 15, wherein said optics includes an aSil.

19. The apparatus of claim 15, wherein said optics includes a beam splitter arranged to:

split a reference beam from the generated beam;

apply the remaining generated beam to said substrate;

apply the reference beam to said optical system; and receive the reflected beam from said substrate for application to said optical system.

20. The apparatus of claim 15, wherein said optical system includes:

reference optics for receiving a portion of the generated beam as a reference beam; and combining optics for combining the reference beam and the reflected beam for application to said sensing means.

21. The apparatus of claim 20, wherein said reference optics includes a quarter wave plate and a polarizer.

22. The apparatus of claim 21, wherein said reference optics includes reflecting means for causing the reference beam to be reflected back through the polarizer and the quarter wave plate to the combining optics.

23. The apparatus of claim 22, wherein the quarter wave plate is aligned to 45 degrees and the polarizer is aligned to zero degrees.

24. The apparatus of claim 15, wherein the reflected beam has a first component unresponsive to the effects of the electrical activity of the substrate at an intensity orders of magnitude greater than a second component therefrom that represents the electrical activity and the optical system provides in the reflected beam applied to the sensing system characteristics that distinguish the first and second components.

25. The apparatus of claim 24, wherein the processing means provides separate signals for the first and second components.

26. The apparatus of claim 15, further including 2D means for causing the reflected beam to represent a two dimensional area of the substrate.

27. The apparatus of claim 26, wherein the 2D means includes scanning means.

28. The apparatus of claim 15, wherein said processing means includes lock in amplifiers and/or balance detectors providing time resolved and DC components from the sensed beams.

29. The apparatus of claim 15, further including means for displaying said indication of the electrical activity in a two dimensional form.

30. Apparatus for dual-phase interferometric confocal imaging for electrical signal modulation mapping in ICs comprising:

a source of laser radiation;

means for dividing a beam of said radiation into a generated beam directed to an IC and a reference beam, and for receiving a reflected beam from the IC;

means for combining said reflected and reference beams;

means for adjusting phase and polarization in said reflected and reference beams; and means for detecting the adjusted reflected and reference beams to provide an indication of electrical activity in said IC.

31. Apparatus for dual-phase interferometric confocal imaging for electrical signal modulation mapping in ICs comprising:

means for splitting a reference beam from a generated beam of laser radiation;

means for applying the remaining generated beam to an IC;

means for receiving a reflected beam of laser radiation from said IC having information representative of electrical activity in said IC;

optical processing means responsive to the reflected beam and the reference beam for creating a plurality of beams having distinct polarization and retardation properties; and means responsive to said plurality of beams for isolation of the information representative of said electrical activity.

32. The apparatus of claim 31, wherein said means responsive to said plurality of beams for isolation of the information representative of said electrical activity includes one or more lock-in amplifiers.

\* \* \* \* \*